(12) United States Patent
Merkin et al.

(10) Patent No.: US 7,464,041 B2
(45) Date of Patent: Dec. 9, 2008

(54) HEALTH CARE ADMINISTRATION METHOD HAVING QUALITY ASSURANCE

(75) Inventors: Richard Merkin, 18107 Sherman Way, Reseda, CA (US) 91335-4564; Mary Inglis, Bakersfield, CA (US)

(73) Assignee: Richard Merkin, Marina Del Rey, CA (US)

( * ) Notice: Subject to any disclaimer, the term of this patent is extended or adjusted under 35 U.S.C. 154(b) by 902 days.

(21) Appl. No.: 10/679,178

(22) Filed: Oct. 3, 2003

(65) Prior Publication Data
US 2005/0010440 A1 Jan. 13, 2005

Related U.S. Application Data

(63) Continuation-in-part of application No. 10/615,640, filed on Jul. 8, 2003.

(51) Int. Cl.
*G06Q 10/00* (2006.01)
*G06Q 50/00* (2006.01)

(52) U.S. Cl. .......................................................... 705/2
(58) Field of Classification Search .................. 705/2–3
See application file for complete search history.

(56) References Cited

U.S. PATENT DOCUMENTS

| | | | |
|---|---|---|---|
| 5,365,425 A * | 11/1994 | Torma et al. ................... | 705/2 |
| 6,067,524 A | 5/2000 | Byerly | |
| 6,240,394 B1 | 5/2001 | Uecker | |
| 6,341,265 B1 | 1/2002 | Provost | |
| 6,343,271 B1 | 1/2002 | Peterson et al. | |
| 6,735,569 B1 | 5/2004 | Wizig | |
| 6,820,058 B2 | 11/2004 | Wood et al. | |
| 6,824,052 B2 | 11/2004 | Walsh | |
| 7,016,856 B1 | 3/2006 | Wiggins | |
| 7,039,458 B2 | 5/2006 | Ueda et al. | |
| 2001/0021910 A1 * | 9/2001 | Goldstein ....................... | 705/2 |
| 2001/0037214 A1 | 11/2001 | Raskin et al. | |
| 2002/0007290 A1 | 1/2002 | Gottlieb | |
| 2002/0019754 A1 | 2/2002 | Peterson et al. | |
| 2002/0026105 A1 | 2/2002 | Drazen | |
| 2002/0035316 A1 * | 3/2002 | Drazen ........................ | 600/300 |
| 2002/0038227 A1 * | 3/2002 | Fey et al. ........................ | 705/3 |
| 2002/0062226 A1 | 5/2002 | Ito | |
| 2002/0072933 A1 * | 6/2002 | Vonk et al. ..................... | 705/2 |

(Continued)

OTHER PUBLICATIONS

Wellmark Health Plan of Iowa. Preventive Care Guidlines. Mar. 6, 2002. p. 1-7. <http://web.archive.org/web/20020603180216/http://www.wellmark.com/health_improvement/blueprints/preventive_care_guidelines.htm>.*

(Continued)

*Primary Examiner*—C Luke Gilligan
*Assistant Examiner*—Sheetal R. Rangrej
(74) *Attorney, Agent, or Firm*—Stetina Brunda Garred & Brucker

(57) ABSTRACT

Methods of health care administration operative to render high quality of health care are disclosed. A patient population is first identified and then information regarding each individual patient within the population is obtained, preferably in an electronic medical record format. Health care is thereafter provided to the patient within the patient population for both acute and chronic conditions according to a health care office scheduling procedure. Preventative health care and care for the treatment of chronic disorders are continuously rendered according to clinically appropriate standards. Extensive patient outreach services are provided to insure appropriate health care is rendered according to all applicable clinically appropriate standards.

14 Claims, 4 Drawing Sheets

U.S. PATENT DOCUMENTS

| | | | |
|---|---|---|---|
| 2002/0120471 A1* | 8/2002 | Drazen | 705/3 |
| 2002/0149616 A1 | 10/2002 | Gross et al. | |
| 2003/0074228 A1 | 4/2003 | Walsh | |
| 2003/0078811 A1 | 4/2003 | Cole et al. | |
| 2003/0078813 A1 | 4/2003 | Haskell et al. | |
| 2003/0078911 A1 | 4/2003 | Haskell et al. | |
| 2003/0154107 A1* | 8/2003 | Medvedeff | 705/2 |
| 2004/0088192 A1* | 5/2004 | Schmidt et al. | 705/3 |
| 2004/0186744 A1 | 9/2004 | Lux | |
| 2004/0249672 A1* | 12/2004 | Bocionek et al. | 705/2 |
| 2006/0080146 A1 | 4/2006 | Cook et al. | |
| 2006/0085222 A1 | 4/2006 | Huang et al. | |

OTHER PUBLICATIONS

Wellmark Bluecross BlueShield. Preventive care programs. Nov. 11, 2001, pp. 1-14. <http://web.archive.org/web/20011006183727/www.wellmark.com/health_improvement/blueprints/preventive_care.htm>.*

Korff, Micheal et al. Collaborative management of chronic illness. Annals of Internal Medicine, Dec. 15, 1997. 127(12), pp. 1097-1102.*

* cited by examiner ns, as well
HEALTH CARE ADMINISTRATION METHOD HAVING QUALITY ASSURANCE

CROSS-REFERENCE TO RELATED APPLICATIONS

The present application is a continuation-in-part of U.S. patent application Ser. No. 10/615,640, filed on Jul. 8, 2003, entitled Health Care Administration Method, the teachings of which are expressly incorporated herein by reference.

STATEMENT RE: FEDERALLY SPONSORED RESEARCH/DEVELOPMENT

Not Applicable

BACKGROUND OF THE INVENTION

The ability to render high quality health care in a cost effective manner is an elusive objective that many health care plans and providers have attempted but very few have actually attained. In this regard, despite substantial effort by health care plans, health maintenance organizations (HMO), physician networks, government-sponsored health care plans and the like, to provide even minimal standards of care, an in particular essential preventative care, such as immunizations and ongoing care for the treatment of chronic diseases, such as diabetes, virtually every attempt made in the art thus far has failed due to gross inefficiencies in the utilization of resources to provide such minimal levels of health care. As a consequence, such plans and programs fail to render all necessary care to the patients sought to be treated, thus resulting a system whereby substandard care is provided and/or patients do not receive necessary preventative care or treatment.

In an attempt to quantify the degree of quality of health care provided by a given health care providing entity, and in particular managed health care plans, numerous quality assurance measures have been implemented that seek to identify the level of care being provided, as well as how such care compares amongst competing health care providers, health care plans, and the like. In this regard, there is an extreme interest amongst consumers and public interest groups in assessing the degree of care administered to patients enrolled in a particular health care plan, particularly with respect to the access patients have to health care providers, the quality of care delivered to such patients, and overall patient satisfaction. Typically, such data is gathered via on-going surveys of patients and their experiences in receiving care from a particular health plan, as well as other statistical data related to the number and types of procedures offered and administered by a particular health care plan, particularly with respect to preventative care and chronic disease management.

While a substantial number of such health care quality assessment programs are administered on a nation wide, state, and local regional levels, the most well-known and widely utilized resource for comparing the performance of health care plans is that generated from the Health Plan Employer Data and Information Set (HEDIS®) survey administered by the National Committee for Quality Assurance (NCQA). In this regard, the NCQA sets standards for the quality of health care and service that health care plans provide to their members and, to the extent a health plan meets certain standards, such plan receives accreditation by NCQA. To that end, NCQA utilizes HEDIS as a set of standardized performance measures designed to evaluate the performance of managed health care plans, with particular emphasis on customer (patient) service, access to care and claims processing. Such survey data is further designed to provide comprehensive data related to a given health care plan's effectiveness to provide preventative care, such as immunizations, as well as delivery of quality care to individuals with chronic illnesses, such as diabetes and cardiovascular disease. Presently, the NCQA's HEDIS database features performance data and member satisfaction information from 267 health plans covering more than 61 million Americans.

Notwithstanding the data available to consumers, as well as any accreditation and/or certification that a given health care plan does provide a requisite level of quality health care, there is still lacking in the art any systematic and uniform manner by which such quality health care can be continuously and systematically delivered. Ironically, although the standards and criteria for providing optimal health care are apparently well-known, particularly with respect to specific types of preventative care and chronic disease management, no single health plan has been able to continuously provide such high quality of care. Lacking even further is any type of systematic approach that can be readily implemented by a given health care plan, HMO, and the like that is operative to not only substantially eliminate inefficient and ineffective health care practices, but consistently achieve an extremely high quality of health care conforming to standardized treatment protocols, particularly with respect to the administration of preventative care and treatment of chronic diseases. There is further a need in the art for such a system that can provide such high quality of health care that is further operative to serve as a profitable business model from which other health care plans and the like can readily emulate such that the high quality delivery of standardized health care, as can be objectively evaluated, can be immediately implemented.

BRIEF SUMMARY OF THE INVENTION

The present invention specifically addresses and alleviates the above-identified deficiencies in the art. In this regard, the present invention is directed to methods of administering standardized types of health care, particularly with respect to preventative care and disease management for a variety of chronic conditions, that is substantially more efficient and cost-effective than prior art practices and is further operative to continuously meet or exceed standardized levels of care as may be promulgated from a health care administration agency, such as the NCQA.

According to a preferred embodiment, a patient population is first identified to which specified health care services will be rendered. The identification of such patient population may take any of a variety of techniques well-known in the art, particularly with respect to the enrollment of individuals within conventional health care plans or HMO's such as Blue Shield, Blue Cross, Kaiser Permanente, and the like. Such patient population may further be identified through such enrollment procedures set forth in Applicants' co-pending U.S. patent application Ser. No. 10/615,640, filed on Jul. 8, 2003, entitled Health Care Administration Method, the teachings of which are incorporated herein by reference. Along these lines, it is contemplated that such patients comprising the patient population may be charged periodic premiums and the like, as per conventional health plan and health insurance practices.

Once enrolled, substantial medical information is compiled with respect to each patient within the patient population to which health care services will be rendered. In this regard, it is contemplated that all relevant data related to the health and medical history of each patient will be closely recorded, particularly with respect as to whether or not any patient presents any type of demographic data indicative of the need for preventative care. For example, specific data will be derived from women within the patent population that are between the ages 50-69 as to whether such patients have had a mammogram and, if so, when such procedure was last performed. Similarly, data will be obtained from those patients within the patient population of age 2 or younger regarding whether or not each such patient has had the appropriate immunizations in the applicable prescribed time frames. Preferably, all such data will be obtained, stored, and periodically updated via the use of Electronic Medical Records (EMR) to thus enable medical data indicative of each of the patients within the patient population to be quickly and easily accessed and updated. Along these lines, it is contemplated that any of a variety of commercially available EMR software products can be utilized in the practice of the present invention.

Once as much data can be obtained from each of the patients within the patient population, on-going health care is administered thereto. With respect to the administration of such health care, the same will preferably take the form of those methods disclosed in Applicants' co-pending U.S. patent application Ser. No. 10/615,640, although other conventional methods for delivering health care are also contributed to be within the scope of the present invention.

In regard to the delivery of such health care, the present invention expressly conditions the administration of the same via two important aspects, the first being directed to health care provided in an office-based setting, and the second being directed to the administration of preventative care and care related to patients afflicted with a chronic condition. With respect to the former, the present invention expressly contemplates that medical services sought to be rendered in an office setting will adhere to a particular schedule whereby patient is seeking preventive care or treatment for a chronic condition will be scheduled in advance for an appointment made during a particular part of the day, preferably morning, and will be expressly coordinated with any and all applicable tests and procedures that are preferably performed concurrently with a particular appointment associated with the treatment of a chronic condition. In this regard, it is expressly contemplated that any and all applicable lab work, x-rays, or other complimentary medical service to be rendered in connection with an office visit related to the treatment of a chronic disease will be concurrently scheduled well in advance to maximize efficiency and closely correlate with any and all procedures that are relevant to the treatment of a particular patient for a given chronic condition. All other matters, which will typically involve treatment of an acute condition, such as an injury, infection, or other typically non-recurring condition, will be scheduled for office visits at alternative times (e.g. the afternoon). In this regard, the present invention expressly contemplates the ability of patients to readily access health care, and in particular to provide the opportunity for a patient to see a primary care physician in an office-based setting as soon as conveniently practical. To achieve that end, it is contemplated that an allotment of time, preferably scheduled in the afternoon, will thus provide the opportunity for patients seeking such health care for non-chronic conditions or non-preventive care to be afforded the opportunity to seek treatment.

With respect to the latter element, namely, the methodology related to providing preventative care and treatment of chronic conditions, the present invention requires systematic and continuous review of the medical data obtained from the patients within the patient population, particularly with respect to those patients either in need of on-going preventative care or who are afflicted with a chronic disease. In both categories, namely preventative care and chronic disease management, the care to be prescribed will be identical to those considered in the art to be most appropriate and may preferably comprise those standards of care expressly set forth in the NCQA's HEDIS criteria or otherwise conform to any other standardized, objective preventative care/chronic disease management treatment protocols to thus set the level of care for which each patient within the patient population will receive. For example, all children within the patient population will be afforded the opportunity to receive all applicable immunizations as deemed objectively appropriate by recognized medical practices. Similarly, all applicable female patients falling within the applicable age category will be afforded all objectively desired breast cancer and cervical cancer screening tests (i.e., mammography and pap smears).

From such data, an initial assessment is made as to which patients within the relevant portions of the patient population have received the necessary preventative care. To the extent such preventative care has been rendered (i.e., immunizations, mammography, etc.), all medical records are appropriately updated. To the extent any particular patient within the patient population has not received the preventative care ideally suited for such patient, an assessment is made as to whether or not such individual is, in fact, eligible for such preventative care, has otherwise received such preventative care from a different health care plan/health care provider, whether or not such preventative care is, in fact, warranted for such individual based upon the individuals unique circumstances.

To the extent a patient scheduled to receive such preventative care has not, in fact, received such care, an outreach program is implemented whereby several attempts are made to contact the particular patient and schedule the appropriate preventative care procedure. In this regard, all conventional practices are utilized to contact the patient to not only alert the patient of the preventative care to be rendered, but to further educate the patient to thus emphasize the importance of the need for such care. Diligent efforts are made until such time as either the preventative care is, in fact rendered, the patient refuses such treatment, or that every attempt to contact the patient has failed. All such outcomes are documented in the patient's medical records. In any event, however, such preventative care or attempts to render the same will preferably strictly conform to the objective treatment criteria set forth in the established medical literature and may preferably take the objective treatment criteria set forth in NCQA's HEDIS guidelines.

A similar approach is utilized with respect to the treatment of chronic diseases. In this regard, all patients identified as having a chronic disease, whether it be diabetes, arthritis, cardio vascular disease or any of the other well-recognized chronic diseases, will be identified via a continuous and systematic review of the patient's medical data. The appropriate medical treatment to be utilized to treat such chronic condition, which again will take the form of any well-recognized objective treatment protocols such as those set forth by the NCQA or other recognized health care standards agency, will be utilized to develop a type of treatment to be rendered. A careful assessment will be made for all patients in need of such treatment to ensure that they have, in fact, received such care. Alternatively, an assessment will be made as to whether or not such patients are eligible to receive such treatment as the same may no longer be applicable. Likewise, efforts will be made to verify whether or not such treatment has been rendered by another health plan or health care provider to thus ensure that such treatment would be duplicative of the care already provided to the patient.

To the extent such scenarios are not applicable, every attempt will be made to contact such patient to ensure the patient receives the adequate degree of care. Such attempts will continuously be made via all conventional practices known in the art until such time as the care has been rendered, the patient refuses such treatment (as will be documented), or all attempts to contact the patient have failed. In all such circumstances, unless the patient has either refused service or has been unable to be reached, the appropriate standard of care will have been rendered to the patient and the objective criteria for disease management will have been met, thus ensuring that a high degree of quality health care has been provided.

BRIEF DESCRIPTION OF THE DRAWINGS

These as well as other features of the present invention will become more apparent upon reference to the drawings.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 1:
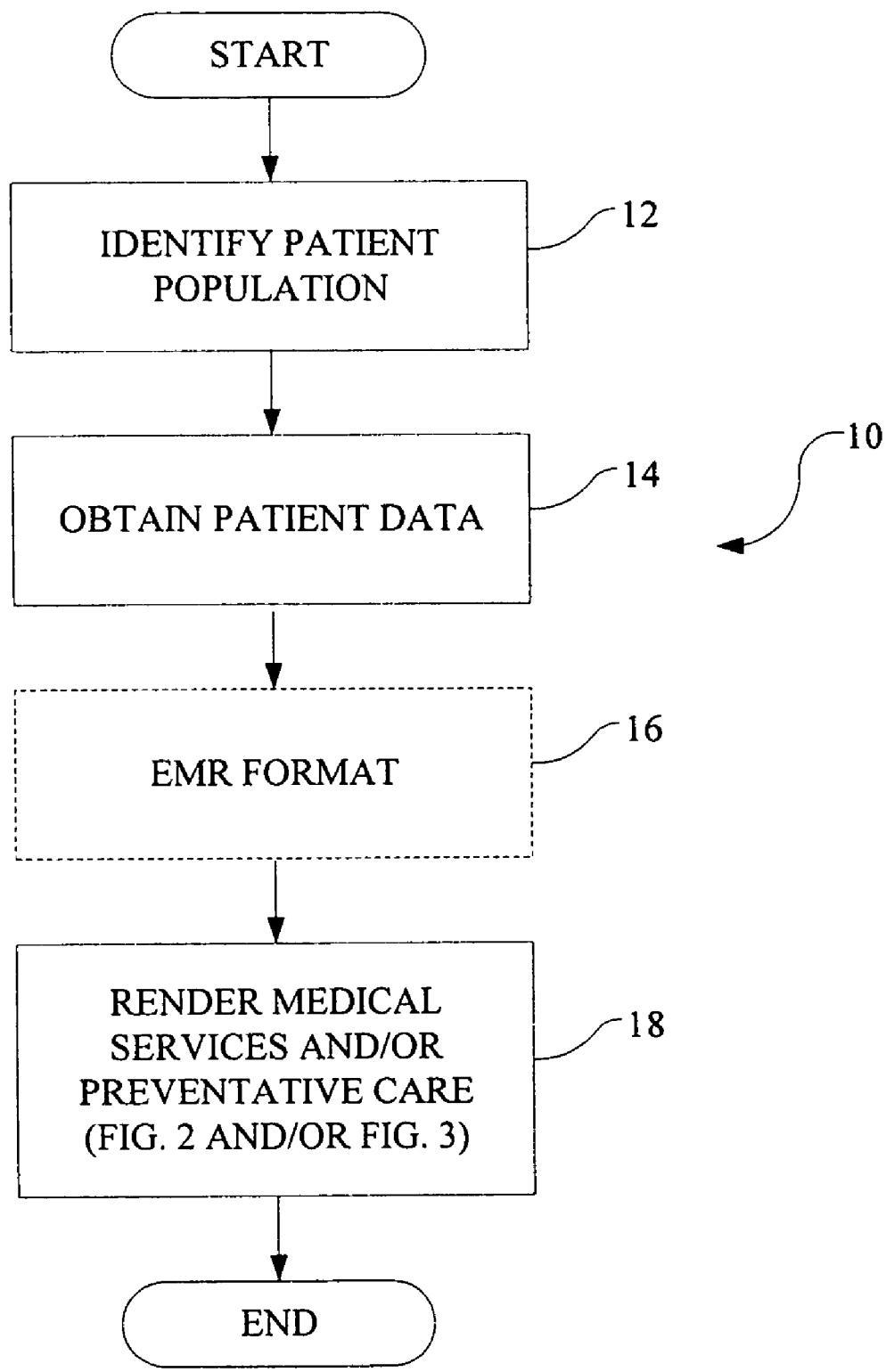
FIG. 1 is a flow chart depicting the steps for identifying and obtaining information from a specific patient population and thereafter rendering medical services and/or preventative care thereto.

Referring now to the drawings, and initially to FIG. 1, there is shown a process 10 for delivering high quality health care that is operative to consistently render care, particularly with respect to preventative care and the treatment of chronic diseases. The process 10 has been proven to deliver health care in a manner that continuously assures that optimal quality is provided to those patients being treated when viewed by objective survey criteria as is frequently utilized in the assessment of consumer satisfaction and the ability of conventional health plans, HMO's and the like to deliver health care. According to the initial step 12, the process comprises the step of identifying a patient population. In this regard, it is expressly contemplated that the present invention will be utilized by conventional health plans, HMO's, government-sponsored health care programs, such as Medicare, as practiced in the United States, and the like. Through such health plan, HMO, etc., care will be rendered to the patient population identified in step 12. To that end, it is contemplated that the patient population will be generated by any of a variety of conventional means (i.e., such as those utilized by HMO's and well-known health plans, such as Blue Shield and Blue Cross.) Along these lines, it is expressly contemplated that the patient population identified in step 12 may be generated and identified pursuant to those methods disclosed in Applicants' co-pending U.S. patent application Ser. No. 10/615,640, incorporated herein by reference. In any event, however, it is contemplated that an ultimate determination will be made as to the number and identity of the specific individuals comprising the patient population, and whether the same are, in fact, entitled to receive health care to be provided pursuant to the methods of the present invention.

Once the patient population has been identified in step 12, significant patient data is then obtained in step 14 from each respective individual within the patient population. Although it is contemplated that a considerable amount of such information will have been previously obtained as part of the application/enrollment procedures employed above in the identification of the patient population in step 12, it is expressly contemplated that to the extent any critical data for each respective patient has not been obtained, the same will be supplemented via step 14. In this regard, it will be understood by those skilled in the art that such patient data will include, at a minimum, the patient's age, sex, ethnicity, medical history, occupation and other demographics. Likewise, such information may include patient pharmacy records and medication compliance. Most importantly, for reasons discussed more fully below, such patient data will expressly include any and all applicable data related to the relevant preventative care that would ideally be rendered to each specific patient within the patient population, whether such care has already been rendered, whether or not each particular individual is afflicted with a chronic medical condition, and what treatment has been rendered to date in relation to the management of such chronic disease. For example, patient data related to the immunization history of all children who are identified within the patient population will be recorded and assessed to insure that the proper preventative care has been rendered. Likewise, data indicative of all breast cancer and cervical cancer screening measures that have been taken for all women within the relevant age groups within the patient population will be obtained and assessed. Similarly, with respect to those patients within the patient population having a chronic disease, such as coronary artery disease, asthma, or diabetes, for example, data will be obtained as to the current state of the health of such individuals, as well as what medical attention has been rendered to date with respect to the treatment of such disease. For example, data from those patients within the patient population who are afflicted with diabetes will be obtained with respect to any and all lab criteria, such as HgbAlC testing, that has been previously rendered up to the time that the patient has been enrolled within the patient population identified in step 12.

In order to expedite the collection of such patient data, and to efficiently assess and monitor the current state of the health of those patients within the patient population identified in step 12, it is contemplated that all conventional medical assessment techniques well-known in the art may be utilized. In particular, it is contemplated that the medical records of the patients within the patient population will be reviewed to determine whether or not such patients have been diagnosed with a particular disease, pursuant to conventional disease classification techniques, and in particular the use of the International Classification of Diseases Ninth Edition (ICD-9) three digit codes. Likewise, with respect to the treatment that has been rendered to such individuals, it is contemplated that, where applicable, all pertinent procedures that have previously been rendered, preferably according to Current Procedural Terminology (CPT) codes will be recorded and assessed to determine whether or not which, if any, standardized procedures have been rendered in relation to the care of a particular patient, particularly with respect to any chronic disease he or she may have.

To facilitate the collection and storage of such patient date collected in step 14, it is expressly contemplated that the same will preferably be collected and stored according to an Electronic Medical Record (EMR) format, as illustrated in step 16. Although optional, it is expressly contemplated that to achieve optimal efficiency of the methods of the present invention EMR software will be utilized to generate electronic medical records, as well as preferably electronic claims filing and other medical management tasks (e.g., managed care and capitation tracking, referral analysis reports, etc.). To that end, it is contemplated that any of a variety of conventional software products can be utilized. Exemplary of such currently-available EMR software include those medical management software products produced by American Medical Software of Edwardsville, Ill.; SoapWare EMR Software, produced by Docs, Inc. of Springdale, Ariz.; and EMR/Medical Practice Management Software produced by Expert Systems Applications, Inc. of Solon, Ohio. Generally, such automated, software driven products are operative to facilitate and increase the efficiency of conventional health care practices, substantially enhance the security associated with patient information, and utilize industry-recognized, standardized formats necessary to conduct and codify medically-related electronic transactions. In this regard, it is expressly contemplated that once all of the patient data is retained in an EMR format, the same will be able to be accessed far more effectively and efficiently, which will thus in turn enhance the methodology of the present invention.

Once all applicable patient date has been collected for those patients in the patient population, on-going care is then provided via step 18. Along these lines, it is contemplated that conventional medical practices will be utilized whereby a variety of medical services and procedures will be routinely provided to patients within the patient population as needed. Preferably, the care to be rendered will substantially conform to those methods of administering health care as set forth in Applicants' co-pending U.S. patent application Ser. No. 10/615,640, particularly with respect to the limited use of CPT codes for identifying the services to be rendered, coupled with the close scrutiny and authorization practices to be utilized therewith to ensure that the most efficient and effective medical care is provided while conserving the utilization of medical resources available to the patients within the patient population.

An extremely important aspect that the present invention does take into consideration, however, is that in the rendering of such medical services and/or preventative care in step 18, the same will be provided in strict accordance with standardized levels of care recognized in the art as may be promulgated by consumer groups, government agencies, or health care administration agencies. It is expressly contemplated that any type of standardized criteria as may be utilized to set the quality of care offered by a particular health plan, HMO, and the like can be relief upon as an appropriate standard of care. In this regard, it is expressly contemplated that the standards by which the care is rendered in step 18 may conform to the HEDIS standardized performance measures implemented by the NCQA, particularly as the same pertains to the standardized levels of preventative care and treatment of chronic diseases. Similarly, the level of care to be rendered in step 18 may further conform with the objective standards of care which must be rendered in order to receive accreditation/certification status by a particular consumer group, government agency, and the like. Along these lines, it is expressly contemplated that the objective standards of rendering care necessary to obtain accreditation/certification of disease management by the NCQA will likely serve as a suitable model by which the medical services to be rendered to the patients within the patient population and will define the appropriate standard of care to be provided. In fact, it is expressly contemplated that the care to be rendered will identically mimic as much as possible the objective standards set forth by an applicable authority, in this case the HEDIS management practices as set forth by the NCQA, so that evaluation of a given health plan, HMO, etc., utilizing the practices of the present invention will at all times meet or exceed the objective standard levels of care defined by such governing authority.

With respect to the delivery of such standardized care, the practices of the present invention utilize two fundamental principles. The first principle is directed to the access patients within the patient population have to seek medical attention in an office-based setting, typically by a primary care physician (PCP). The second principle, discussed more fully below, implements a delivery of care that is specific towards achieving an optimal degree of preventative care and treatment of chronic diseases such that the level of care is consistently administered according to recognized, objective criteria.

Figure 2:
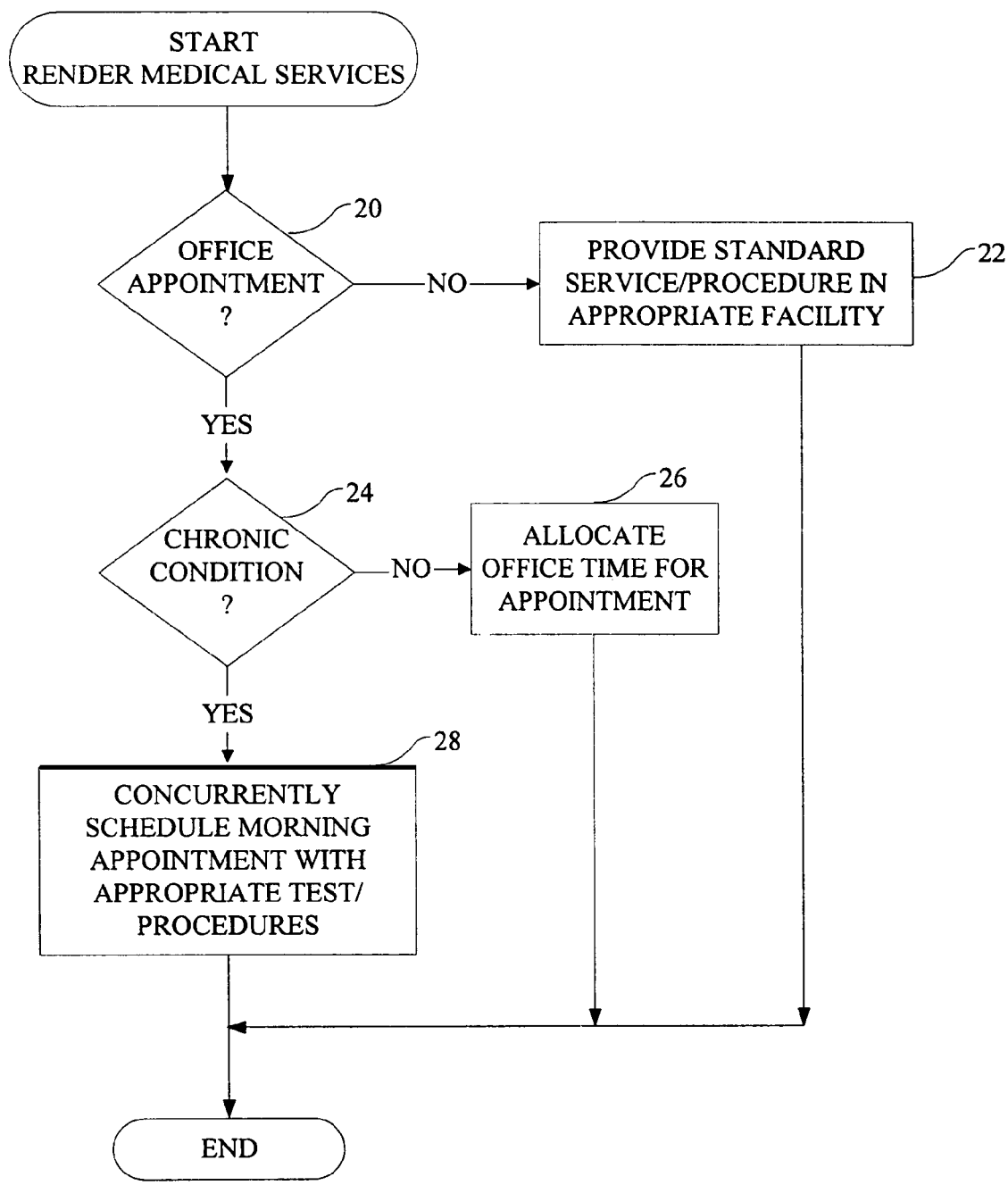
FIG. 2 is a flow chart depicting the steps for rendering medical services via health care office scheduling practices according to a preferred embodiment of the present invention.

With respect to the former, namely, the accessibility patients have to seek medical treatment in an office-based setting, there is depicted in FIG. 2 a procedural framework for ensuring that optimal accessibility is provided. According to such methodology, an initial assessment is made as to whether or not the medical services sought to be rendered for a particular patient can be provided in an office-based setting in step 20. As discussed above, to the extent the practices of administering health care pursuant to the present invention conform to those of Applicants' co-pending U.S. patent application Ser. No. 10/615,640, which relies extensively upon the initial evaluation by a PCP, an office appointment will typically be necessary to provide the desired degree of care. In those situations where an office appointment is inapplicable, the appropriate medical care is rendered at the appropriate facility in step 22, such as an emergency room, surgical center or any other appropriate facility where such care must be rendered.

On the other hand, to the extent an office appointment is warranted, which will likely be the majority of the instances where care is sought, a determination is made as to whether or not the purpose for the office visit is for the treatment for a chronic condition 24, which as discussed above may include diseases such as cardio vascular disease, diabetes, asthma and the like, or whether or not the purpose of the office visit is for the treatment of an acute or non-chronic condition such as an injury, infection, or any other type of disease not requiring on-going evaluation and treatment.

With respect to either of such conditions, whether they be chronic or acute in nature, it is contemplated that dedicated office times will be set aside such that all patients being treated for a chronic condition are seen at one particular time whereas all patients being seen for an acute or non-chronic condition are seen at a separate time. With respect to those patients being seen in relation to the treatment of a chronic condition, such appointments will be scheduled at a particular time of day, and preferably in the morning via step 28, to thus enable any and all types of concurrent procedures, such as lab work, X-rays, and the like, to likewise be concurrently scheduled to thus optimize efficiency and enable patient care to be comprehensively rendered via a single visit.

Along these lines, it is contemplated that those patients being treated with a chronic condition will thus require predictable, on-going treatment, and that scheduling any and all office visits, as well as all applicable tests and procedures to be rendered in connection therewith, can be done so sufficiently far in advance to allow for the coordination and arrangement of office visits in connection with any and all ancillary medical services to be rendered in connection with a particular patient. It should be readily understood by those skilled in the art, however, that although the present invention contemplates that it may be preferable to arrange for the appointment of office visits for those afflicted with chronic diseases in the morning, any and all scheduling alternatives are likewise contemplated to fall within the scope of the present invention. For example, it is contemplated that chronic patients may be scheduled for afternoon office visits, or may otherwise be scheduled for one or more particular days of the week or may be assigned to particular days or a dedicated week within a month so that all such chronic patients can be sequentially seen via appointments scheduled around a common time frame.

With respect to those patients seeking an office visit for an acute or non-chronic condition, it is likewise contemplated that dedicated times will be provided so that all such patients seeking medical attention have prompt access to medical attention. To that end, it is contemplated that patients in need of such treatment can make an appointment within an allocated office time for such appointments in step 26. Although it will be recognized by those skilled in the art that the office time is allocated may be set for particular days of the week or for only certain times in a given month, it is contemplated that providing a daily allotment of office time to see patients in need of medical treatment for an acute or non-chronic disease will result in substantially higher patient satisfaction, as well as a higher degree of medical care by thus enabling a patient having a particular condition to be readily seen, preferably to the extent the patient needs to make an appointment on the same day basis or within a 24 hour period. In this regard, any system which imposes any type of substantial delay limiting a patient's ability to be seen by his or her PCP in an office-based setting will be deemed to detract from the principles of the present invention.

Figure 3:
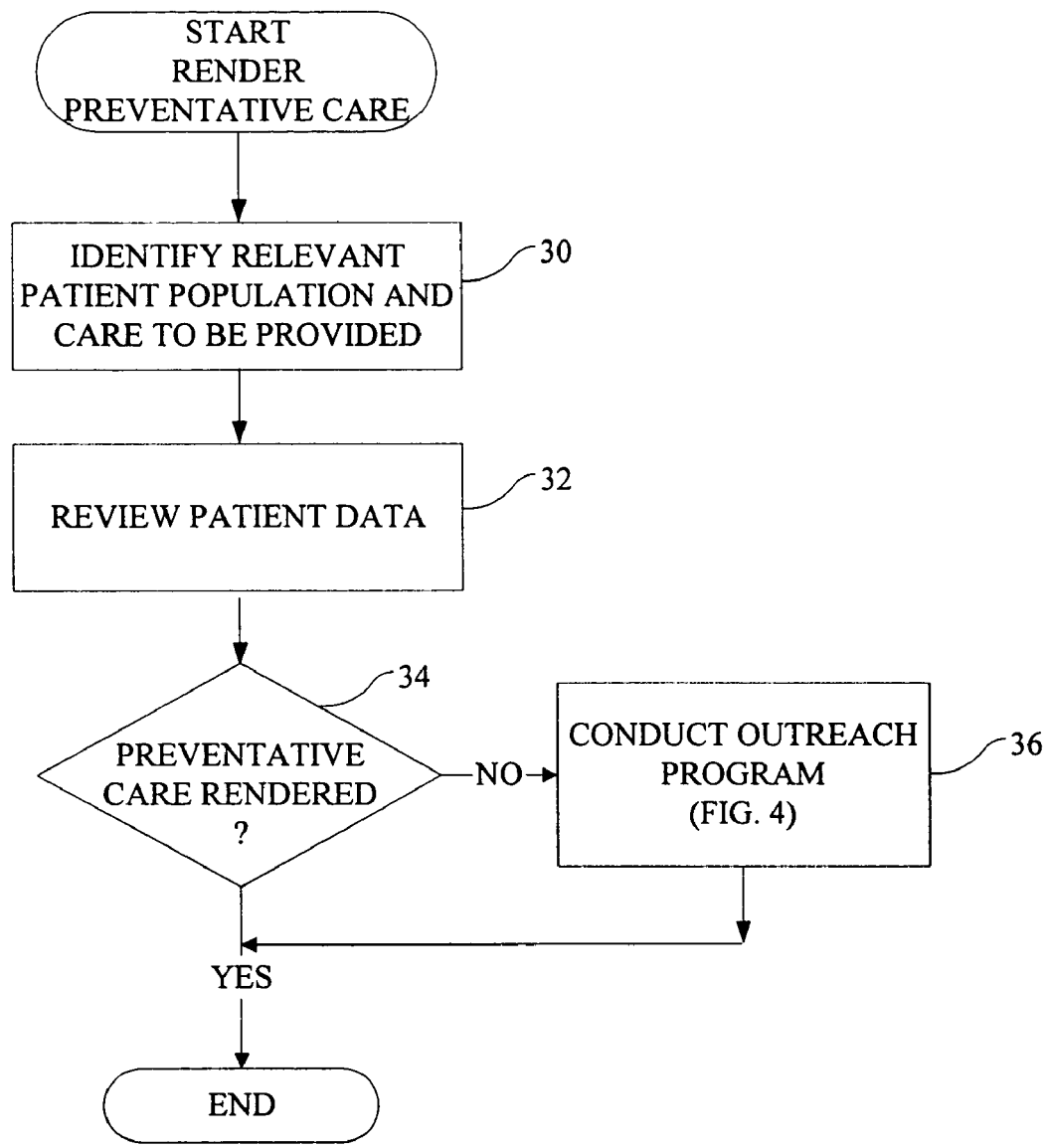
FIG. 3 is a flow chart depicting the steps for rendering preventative care to a known patient population according to a preferred embodiment of the present invention.

Turning now to FIG. 3, there is illustrated the methodology for rendering preventative care to patients within the patient population. Preferably through the framework discussed above through scheduling of office-based appointments, preventative care will continuously be rendered according to those objective standards deemed to be optimal in the art to patients within the patient population. To achieve that end, an identification is first made in step 30 with regard to those patients within the patient population which meet the criteria to receive applicable preventative care. At the outset, it will be recognized that any such preventative care to be provided will strictly conform to those medical practices deemed medically necessary to ensure optimal patient health. Exemplary of such types of preventative care will be readily apparent to those skilled in the art, and will expressly include immunizations for children within the patient population for ages 2 and under, breast cancer screening for women ages 50-69 within the patient population and cervical cancer screening for all women ages 18-64 within the patient population.

To the extent an applicable type of preventative care is to be provided, the patient data previously obtained ins step 14 is periodically reviewed in step 32 to determine whether or not such preventative care is warranted, and if so whether or not such preventative care has been rendered via step 34. In making such determination, it is expressly contemplated that HEDIS criteria can and likely will be utilized to determine if and when such preventative care is to be rendered. To the extent such care is to be rendered, the applicable appointments are made and preventative care administered per conventional practices. Importantly, it is expressly contemplated that all preventative care sought to be rendered will be carefully documented and that where applicable all acceptable codes indicative of care to be rendered will be utilized in documenting the preventative care administered. For example, to the extent HEDIS criteria is utilized in the administration of preventative care related to breast cancer screening, cervical cancer screening and/or childhood immunizations, not only will HEDIS criteria be utilized, but HEDIS identified acceptable codes will be utilized in documenting the degree of preventative care provided to thus ensure that care rendered according to HEDIS criteria has, in fact, been rendered.

As a consequence, by using both HEDIS criteria and identified acceptable codes to document that such criteria has been met, objectively verifiable, high-quality health care will continuously be rendered and readily documented. Along these lines, the data collected as part of the documentation of preventative care that is rendered will be able to statistically verify that all the patients within the patient population have been provided with an optimal degree of high-quality medical care. Indeed, to the extent such health care is not rendered, diligent efforts will be made via an outreach program, identified in step 36 discussed more fully below, to ensure that every effort is made to provide the applicable preventative care.

As will be readily appreciated by those skilled in the art, although the methodology depicted in FIG. 3 references preventative care, the same principles apply equally to the ongoing treatment of chronic diseases. In this context, step 30 will identify all patients within the patient population suffering from a chronic condition and what types of standardized care should be rendered to patients treated with a particular condition, which again may utilize HEDIS criteria or any other objective medical treatment protocol. Patient data will be reviewed in step 32 and a determination made in step 34 as to whether or not a particular procedure or treatment is to be rendered to a particular individual. For example, for patients afflicted with diabetes, routine hemoglobin A1C (HgBA1c) testing will likely be warranted. In such circumstances, the routine performance of such procedures, as set forth by HEDIS criteria, will determine the number of office visits and tests to be rendered in relation to such particular patient to thus ensure that optimal health care is, in fact, provided. To the extent such ongoing treatment for a chronic condition is not rendered, an outreach program 36 will be implemented to ensure that optimal medical care is ultimately provided to the patient in need thereof.

Figure 4:
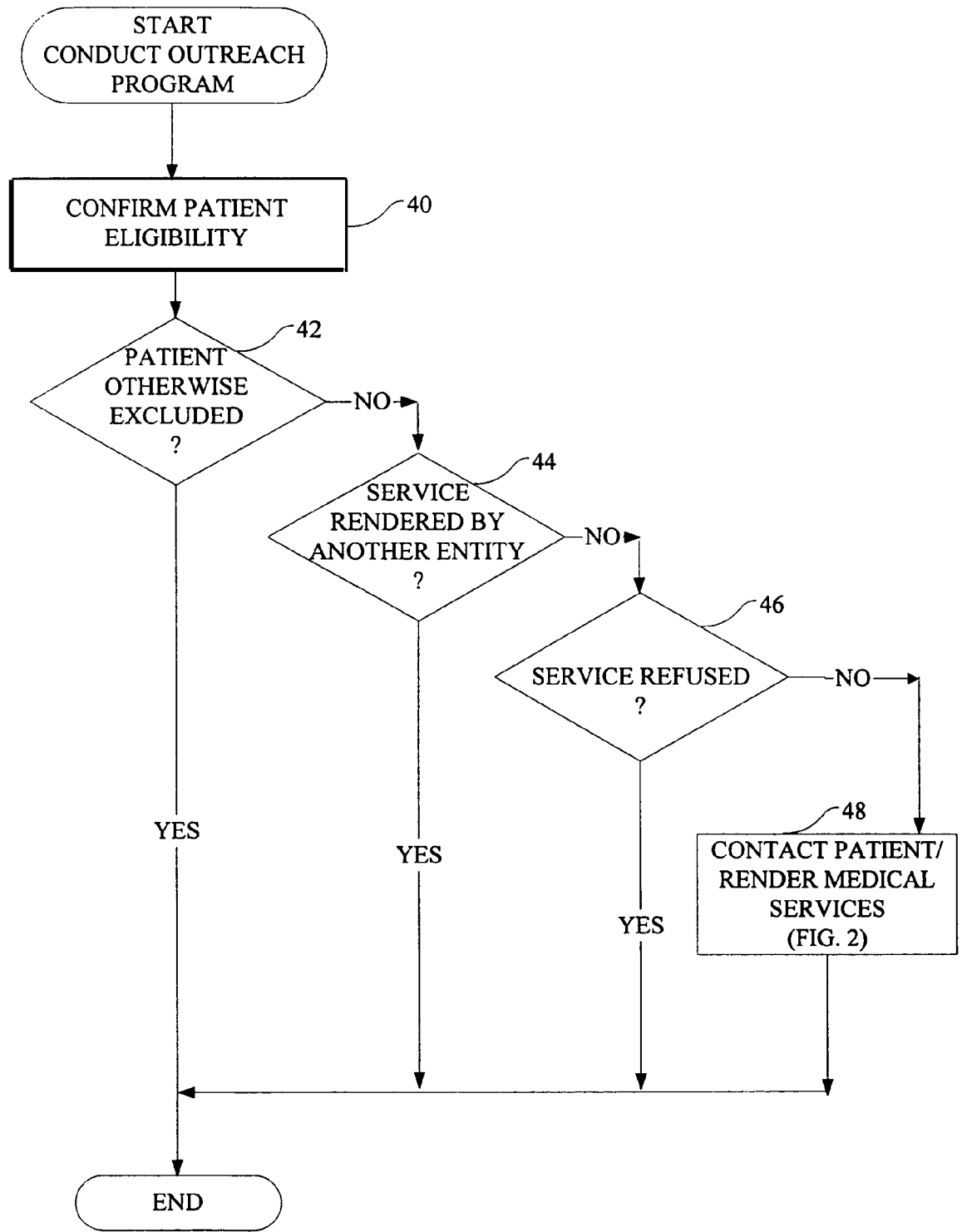
FIG. 4 is a flow chart depicting the steps for maximizing the degree of care rendered to eligible patients within a patient population so as to maximize the number of patients to be provided health care and to insure that an applicable standard of care is obtained for such eligible patients.

To make sure that every reasonable attempt is made to render the appropriate care to those patients within the patient population, there is provided as part of the present invention an outreach program, depicted in FIG. 4, that serves to encourage patients to seek the necessary care, confirm whether or not such patients are still eligible to receive such care whether such patients have been provided with the same or similar type of care from another health care plan, HMO, etc., or otherwise document that the patient has either been unable to be contacted or has otherwise refused treatment. As illustrated, initial step 40 of such outreach program involves confirming whether or not the patient is eligible to receive the necessary care. As per conventional health plan practices, it will be necessary to determine when the patient became enrolled within the patient population and whether or not the care to be rendered, which again will preferably conform to HEDIS criteria or other well-recognized standard of care, is appropriate for such patient given the particular timing the patient has been enrolled within the patient population.

To the extent the patient is eligible to receive a particular type of care, whether it be preventative care, treatment of a chronic condition, or any other type of care, decisions made in step 42 as to whether the patient would still be excluded from receiving a particular type of treatment. For example, a female patient that has undergone bilateral mastectomy or has had two unilateral mastectomies would appropriately be excluded from receiving preventative care related to breast cancer screening. Accordingly, the outreach program implemented to provide care to such patient who would otherwise be eligible thus ends.

On the other hand, to the extent the patient is not eligible and otherwise excluded, an assessment is made as to whether or not the particular treatment of care to be provided has been rendered by another entity (i.e., health care plan, HMO, etc.) via step 44. To the extent the applicable medical care has been rendered, the patient's medical records will be updated accordingly to indicate that the care has been provided, at which point the outreach program ends.

If, however, the patient is still eligible, not excluded, and has still not had the appropriate medical services rendered by another entity, a determination is then made in step 46 as to whether or not the patient is consciously avoiding or otherwise refusing the appropriate care to be rendered. In such circumstances where the patient refuses service, such refusal is documented in the patient's medical records. Along these lines, it is contemplated that attempts will be made to persuade the patient to have the services rendered by utilizing conventional communications means, whether it be through telephone calls, letters, e-mail or any other type of methodology known in the art. Once it is confirmed that the services have been refused, the patient's medical records.

Lastly, to the extent none of the foregoing exceptions apply, every reasonable effort will be made via step 48 to contact the patient and render the applicable services, whether it be preventative care, the treatment of a chronic condition, or any other type of condition requiring on-going medical attention. As discussed above, attempts will be made to contact the client through conventional communications means and, unless the patient expressly refuses services via the determination made in step 46, the appropriate medical services to be rendered will be scheduled and ultimately performed. Lastly, to the extent the patient cannot be contacted after all reasonable and diligent efforts have been made, all attempts to contact the patient in order to render the applicable services will be documented to at least evidence that such care was to have been rendered in a timely manner according to the relevant criteria.

Such outreach program will further preferably be implemented on a continuous basis to thus enable high-quality care to be consistently delivered, as well as made accessible to all patients within the patient population in need of such care. As will be appreciated by those skilled in the art, the methodology of the present invention will be readily adapted to ongoing changes in medicine and that the standard of preventative care or treatment of chronic diseases will of course fluctuate with improvements in medical care, medications, and the like. In all such circumstances, however, it will be understood that the criteria set for providing such care will always be deemed to be available and will set the standard by which the care to be rendered to patients within the patient population will be readily identified.

As a consequence of following the aforementioned methodology of the present invention, it is contemplated that any type of health care plan, HMO, physician network, and the like implementing the same can consistently and readily achieve an objectively verifiable system by which health care can be rendered to patients within a patient population. In this regard, so long as the criteria, such as the HEDIS criteria, are utilized in all aspects of the delivery of care, it will thus be in place a standard of care which will be continuously provided. As a further consequence, it is contemplated that any health plan, HMO, and the like implementing the methods of the present invention can specifically tailor the quality of health care provided thereby that will expressly adhere to the criteria set forth by a given quality assessment program and/or health care accreditation/certification standard, thus ensuring that all applicable surveys and/or data generated assessing the quality delivered by such health care plan attains optimal ratings.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A method of administering health care to a population of patients in need thereof, said method comprising the steps:
   a. identifying a patient population entitled to receive said medical care;
   b. determining a standardized criteria of care to be provided to said individuals identified in step (a), the standardized criteria of care including both preventive treatment criteria of care for the preventive treatment of disease, and chronic disease treatment criteria of care for the treatment of chronic disease;
   c. obtaining data from patients identified in step (a), storing such data in electronic medical records embodied on a computer readable medium, and evaluating from such data:
      (i) whether each of said patients fits a preventive treatment profile indicating the need for preventive treatment;
      (ii) whether each of said patients fits a chronic disease treatment profile indicating the need for chronic disease treatment; and
      (iii) for each patient that is in need of either preventive treatment or chronic disease treatment, determining whether each of said patients has received health care services commensurate with either the preventive treatment criteria or chronic disease treatment criteria provided in step (b) according to Current Procedural Technology codes, and identifying those patients in need of either preventive treatment or chronic disease treatment who have not received health care services substantially conforming to said preventive treatment criteria or chronic disease treatment criteria identified in step (b);
   d. for those patients in need of preventive treatment that have not received health care services substantially conforming to said preventive criteria:
      (i) determining the preventive treatment services that are needed for compliance with the preventive criteria according to Current Procedural Technology codes and scheduling the needed preventive treatment services for the patient; and (ii) evaluating patient compliance with the preventive treatment services to determine whether the patient is in need of an outreach program to increase compliance with the preventive treatment, and providing such outreach program to the patient if the patient is in need of the outreach program by identifying those patients who:
1. have received said preventative treatment services identified in step (d)(i);
2. are inappropriate candidates to receive said preventative treatment services identified in step (d)(i);
3. have refused said preventative treatment services identified in step (d)(i); and
4. have not received such medical services and are eligible to receive such services;
contacting those individuals identified in step (d)(ii)(4) to arrange to render said preventive treatment services identified in(d)(i); and
documenting said contacting;
e. for those patients in need of treatment of chronic disease that have not received health care services substantially conforming to said chronic disease treatment criteria:
(i) determining the chronic disease treatment services that are needed for compliance with the chronic disease criteria according to Current Procedural Technology codes and scheduling the chronic disease treatment services for the patient, wherein scheduling for the chronic disease treatment services includes concurrently scheduling needed doctor's appointments with the scheduling of needed test procedures by identifying those patients who:
1. have received said chronic disease treatment services identified in step (e)(i);
2. are inappropriate candidates to receive said treatment identified in step (e)(i);
3. have refused said treatment identified in step (e)(i); and
4. have not received such chronic disease treatment services and are eligible to receive such services;
contacting those individuals identified in step (e)(i)(4) to arrange to render said treatment identified in step (e); and
documenting said contacting;
f. updating the electronic medical records for each patient to reflect any of the preventive treatment services, chronic disease services, and outreach services rendered in steps (d)-(e); and
g. continuously repeating steps (a)-(f),
whereby health care services substantially conforming to the standardized criteria of care are provided to the patient population.

2. The method of claim 1 wherein in step (b), said standardized criteria of care substantially conforms to criteria established by the National Committee for Quality Assurance.

3. The method of claim 1 wherein said preventive care services comprises health care services selected from the group consisting of childhood immunizations, breast cancer screening and cervical cancer screening.

4. The method of claim 1 wherein said step (g) is repeated on at least an annual basis.

5. The method of claim 1 wherein said chronic disease treatment is for the treatment of a chronic disease that is selected from the group consisting of cardio vascular disease, diabetes and asthma.

6. The method of claim 1 wherein in step (d)(ii), said step further comprises identifying all patients within said patient population who refuse to receive the preventive treatment services that are needed for compliance with the preventive treatment criteria, and wherein in step (f) said step further comprises generating an electronic medical record evidencing those individuals identified in step (d)(ii) who have refused to receive said services.

7. The method of claim 1 wherein in step (d), said preventive treatment services are rendered in an office of a primary care physician during a pre-determined time frame.

8. The method of claim 7 wherein said pre-determined time frame comprises a daily allotment of time extending from six A.M. to noon.

9. The method of claim 1 wherein in step (e), said chronic disease treatment services are rendered in an office of a primary care physician during a pre-determined time frame.

10. The method of claim 9 wherein said pre-determined time frame comprises a daily allotment of time extending from six A.M. to noon.

11. The method of claim 1 wherein the preventative treatment services comprise childhood immunizations; and wherein in step (c)(i), the patients that fit the preventive treatment profile comprise children two years of age or younger; and wherein in step (c), said data is obtained from the parents or guardians of such children ages two or under; and wherein step (d)(ii) comprises contacting said parents or guardians of said children ages two or younger to arrange for said childhood immunizations.

12. The method of claim 1 wherein the preventative treatment services comprise breast cancer screening and wherein in step (c)(i) the patients that fit the preventive treatment profile comprise females between the ages of 50-69.

13. The method of claim 1 wherein the preventative treatment services comprise cervical cancer screening and wherein in step (c)(i) the patients that fit the preventive treatment profile comprise females between the ages of 18-64.

14. The method of claim 1 wherein the chronic disease treatment services are to treat a chronic disease selected from the group consisting of cardio vascular disease, diabetes and asthma; and wherein in step (c)(ii) the patients that fit the chronic disease treatment profile are those who are afflicted with a chronic disease selected from the group consisting of cardio vascular disease, diabetes and asthma.

* * * * *